United States Patent [19]

Tsuchida et al.

[11] Patent Number: 5,705,370
[45] Date of Patent: *Jan. 6, 1998

[54] PROCESS FOR PRODUCING L-AMINO ACIDS BY FERMENTATION

[75] Inventors: Takayasu Tsuchida; Haruo Uchibori; Hiroshi Takeuchi; Mitsuyoshi Seki, all of Kawasaki, Japan

[73] Assignee: Ajinomoto Company, Inc., Tokyo, Japan

[*] Notice: The term of this patent shall not extend beyond the expiration date of Pat. No. 5,294,547.

[21] Appl. No.: 440,467

[22] Filed: May 12, 1995

Related U.S. Application Data

[63] Continuation of Ser. No. 35,087, Apr. 12, 1993, abandoned, which is a continuation of Ser. No. 758,509, Sep. 6, 1991, Pat. No. 5,294,547, which is a continuation of Ser. No. 464,385, Jan. 12, 1990, abandoned.

[30] Foreign Application Priority Data

Jan. 13, 1989 [JP] Japan .................................. 1-06955

[51] Int. Cl.$^6$ ............................ C12P 13/06; C12P 13/04; C12P 13/10
[52] U.S. Cl. .................... 435/106; 435/116; 435/840; 435/107; 435/110; 435/114; 435/115; 435/252.1; 435/843
[58] Field of Search ........................ 435/106, 107, 435/110, 114, 115, 116, 252.1, 843, 840

[56] References Cited

U.S. PATENT DOCUMENTS

| | | | |
|---|---|---|---|
| 3,096,252 | 7/1963 | Motozaki et al. | 435/840 X |
| 3,117,915 | 1/1964 | Shiio et al. | 435/840 X |
| 3,660,235 | 5/1972 | Okumura et al. | 435/108 |
| 3,716,453 | 2/1973 | Okumura et al. | 435/107 |
| 3,875,001 | 4/1975 | Kubota et al. | 435/107 |
| 3,878,044 | 4/1975 | Kubota et al. | 435/114 |
| 4,224,409 | 9/1980 | Nakamori et al. | 435/107 |
| 4,389,483 | 6/1983 | Hiraga et al. | 435/110 |
| 4,656,135 | 4/1987 | Tsuchida et al. | 435/116 |

OTHER PUBLICATIONS

Goodfellow et al. "The Biology of the Actinomycetes" 1984, p. 77–79.

Primary Examiner—Irene Marx
Attorney, Agent, or Firm—Oblon, Spivak, McClelland, Maier & Neustadt, P.C.

[57] ABSTRACT

Culturing an L-amino acid producing microorganism belonging to the genus Brevibacterium or Corynebacterium and having a resistance to a peptide containing glutamic acid or aspartic acid gives L-amino acids in high yield.

4 Claims, No Drawings

PROCESS FOR PRODUCING L-AMINO ACIDS BY FERMENTATION

This application is a Continuation of application Ser. No. 08/035,087 filed on Apr. 12 1993, (abandoned), which is a Continuation of Ser. No. 07/758,509, filed on Sep. 6, 1991, (now U.S. Pat. No. 5,294,547), which is a Continuation of Ser. No. 07/464,385, filed on Jan. 12, 1990, abandoned.

BACKGROUND OF THE INVENTION

1. Field of the Invention

The present invention relates to a process for producing L-amino acids by fermentation and microorganisms for producing L-amino acids.

2. Discussion of the Background

L-amino acids have been widely used as seasonings, medical drugs, feed additives, chemicals, reagents and the like. L-amino acids, which are produced by fermentation on an industrial scale, include L-glutamic acid, L-lysine, L-glutamine, L-arginine, L-phenylalanine, L-alanine, L-threonine, L-isoleucine, L-histidine, L-proline, L-valine, L-serine, L-ornithine, L-citrulline, L-tyrosine, L-tryptophan and L-leucine, etc. As microorganisms utilized for the production of L-amino acids, there are those belonging to the genus Brevibacterium, the genus Corynebacterium, the genus Bacillus, the genus Escherichia, the genus Seratia, the genus Providencia, and the genus Arthrobacter, etc.

It is important to produce L-amino acids at low costs on an industrial scale by enhancing the fermentation yield and accumulation of L-amino acids. To produce L-amino acids industrially at low costs utilizing these various microorganisms, improved breeding of microorganism has often been used. That is, the L-amino acid production of wild strains per se is extremely poor in many instances, and therefore, methods for imparting nutrient auxotrophy, imparting analog resistance or imparting nutrient auxotrophy in combination with analog resistance, through artificial mutation; or potentiating a gene for amino acid biosynthesis, etc. by genetic recombination, and the like are used to increase the L-amino acid productivity of the wild strain. However, fermentation with conventional strains does not produce L-amino acids in a sufficiently high yield.

Thus, there remains a need for a process which will produce L-amino acids by fermentation in high yield. There also remains a need for microorganisms which produce L-amino acids in high yield.

SUMMARY OF THE INVENTION

Accordingly, it is an object of the present invention to provide a process for producing L-amino acids in high yield by fermentation.

It is another object of the present invention to provide microorganisms which produce L-amino acids in high yield by fermentation.

These and other objects, which will become apparent during the course of the following detailed description, have been achieved by the inventors' discovery that culturing strains having a resistance to a peptide containing glutamic acid or aspartic acid of the formula x-glu, glu-x, x-asp or asp-x, in which x represents an amino acid, produces L-amino acids in improved yields.

That is, one embodiment of the present invention is a process for producing an L-amino acid, which comprises culturing an L-amino acid-producing microorganism belonging to the genus Brevibacterium or the genus Corynebacterium and having a resistance to a peptide containing glutamic acid or aspartic acid in a liquid medium, for a sufficient time to accumulate the L-amino acid in the culture, and collecting the L-amino acid from the culture.

In another embodiment, the present invention relates to L-amino acid-producing microorganisms belonging to the genus Brevibacterium or the genus Corynebacterium and having a resistance to a peptide containing glutamic acid or aspartic acid.

DETAILED DESCRIPTION OF THE PREFERRED EMBODIMENTS

The term L-amino acid as used herein includes L-glutamic acid, L-glutamine, L-lysine, L-arginine, L-phenylalanine, L-threonine, L-isoleucine, L-histidine, L-proline, L-valine, L-serine, L-ornithine, L-citrulline, L-tyrosine, L-tryptophan and L-leucine, etc. The present invention can even be applied to L-amino acids other than those exemplified herein so long as they are L-amino acids which can be produced by fermentation.

Examples of the peptide of the present invention include tyr-glu, ala-glu, trp-glu, met-glu, gly-glu, glu-gly, glu-leu, glu-his, gly-asp, ala-asp, asp-gly, etc. Strains having a resistance to at least one of these are referred to as peptide-resistant strains in the present invention.

The microorganism belonging to the genus Brevibacterium or the genus Corynebacterium which can be used in the present invention is a variant having the peptide resistance described above and capable of producing an L-amino acid.

To obtain the variants of the present invention, the peptide resistance described above may be induced in the parent strains described below; alternatively, the peptide resistance may also be induced in variants capable of producing an L-amino acid.

Wild strains which can be the parent strains of the variants of the present invention include bacteria belonging to the genus Brevibacterium or the genus Corynebacterium such as a Coryneform producing L-glutamic acid, and are exemplified by the following bacteria.

*Brevibacterium flavum* ATCC 14067
*Brevibacterium lactofermentum* ATCC 13869
*Brevibacterium divaricatum* ATCC 14020
*Brevibacterium saccharolyticum* ATCC 14066
*Corynebacterium glutamicum* ATCC 13032
*Corynebacterium acetoacidophilum* ATCC 13870

For the mutation of these parent strains to the variants of the present invention, a conventional method such as a treatment with N-methyl-N'-nitro-N"-nitrosoguanidine, etc. can be used. Isolation of the variants of the present invention from the mutation-treated bacterial solution can be effected by collecting the strains which can grow in a medium containing the peptide.

Media used for culturing such variants are any conventional media containing carbon sources, nitrogen sources, inorganic ions, substances satisfying nutrient auxotrophy and, if necessary, other organic trace nutrients including vitamins, etc. As carbon sources, there are preferably used carbohydrates such as glucose, sucrose, etc., organic acids such as acetic acid, etc. As nitrogen sources, there are preferably used ammonia water, ammonia gas, ammonium salts, etc. As inorganic ions, potassium ions, sodium ions, magnesium ions, phosphate ions, and the like are appropriately added to the media, as required. Incubation is preferably conducted under aerobic conditions. When the incubation is carried out while adjusting the pH of the medium to a range from 4 to 8, preferably 5 to 7.5, at a temperature of from 25° C. to 37° C., preferably 28° to 34° C., better results can be obtained. Thus, when the present strains are cultured for 1 to 7 days, remarkable amounts of L-amino acids are produced and accumulated in the media. Subsequently using a collecting method using an ion exchange resin, etc., yields crystals of L-amino acid.

Other features of the invention will become apparent in the course of the following descriptions of exemplary embodiments which are given for illustration of the invention and are not intended to be limiting thereof.

EXAMPLES

An example for the mutation of the parent strains to the variants of the present invention and the relationship between the peptide concentration and degree of growth of the present strains are shown below.

Method for Mutation.

Bacterial cells of *Brevibacterium flavum* ATCC 14067, which has been grown in a bouillon agar slant at 30° C. for 24 hours, were suspended in M/30 phosphate buffer solution at a cell density of $10^9$/ml. To the cell suspension was added 200 µg/ml of N-methyl-N'-nitro-N"-nitrosoguanidine. The mixture was maintained at 0° C. for 20 minutes followed by centrifugation. The cells were inoculated on a medium having the composition shown in Table 1 and cultured at 31.5° C. for 2 to 10 days.

TABLE 1

| Composition of Medium | |
|---|---|
| Component | Content |
| Glucose | 1.0 g/dl |
| Urea | 0.2 g/dl |
| $KH_2PO_4$ | 0.1 g/dl |
| $MgSO_4 \cdot 7H_2O$ | 0.1 g/dl |
| $FeSO_4 \cdot 7H_2O$ | 0.002 g/dl |
| $MnSO_4 \cdot 7H_2O$ | 0.002 g/dl |
| Biotin | 100 µg/l |
| Thiamine hydrochloride | 100 µg/l |
| tyr—glu | 0.5 g/dl |
| Agar | 2.0 g/dl |
| | (pH 7.0) |

From 20 tyr-glu-resistant strains grown in the agar medium, *Brevibacterium flavum* AJ 12418 (FERM BP-2205) was obtained and characterized as having high productivity of L-glutamine.

By procedures similar to the mutation above, strains having more improved productivity of amino acids could be obtained using various amino acid-producing strains as the original strain. Representative examples are shown in Table 2.

In addition to the improvement of bacteria capable of producing glutamine, lysine, arginine, glutamic acid, histidine, proline, isoleucine, etc. illustratively shown in Table 2, the present process is also effective for phenylalanine, threonine, valine, ornithine, tryptophan, citrulline, leucine, tyrosine, and serine.

The peptide resistance of the thus-obtained variants was compared with that of the parent strains.

Onto a liquid medium composed of 0.5 g/dl of glucose, 0.2 g/dl of urea, 0.15 g/dl of ammonium sulfate, 0.3 1 g/dl of $KH_2PO_4$, 0.1 g/dl of $K_2HPO_4$, 0.01 g/dl of $MgSO_4 \cdot 7H_2O$, 0.1 mg/dl of $CaCl_2 \cdot 2H_2O$, 100 µg/l of biotin, 100 µg/l of thiamine hydrochloride, 0.002 g/dl of $FeSO_4 \cdot 7H_2O$, 0.002 g/dl of $MnSO_4 \cdot 7H_2O$ and the peptide in the amounts shown in Tables 3–9 and adjusted to a pH of 7.0, there were inoculated suspensions of each of the cells in sterile water, which were obtained by culturing in natural medium (1 g/dl of peptone, 1 g/dl of yeast extract and 0.5 g/dl of NaCl, pH 7.0) in slants for 24 hours. After culturing for 24 hours, the turbidity associated with the growth of bacteria was determined and the degree of growth is expressed in terms of relative growth degree (%) in Tables 3 through 9.

TABLE 2

| Amino Acid | Parent Strain | Peptide Resistance | Strain Having Improved Yield Based On Glucose |
|---|---|---|---|
| Glutamine | Brevibacterium flavum ATCC 14067 | tyr—glu | Brevibacterium flavum AJ 12418 (FERM BP-2205) |
| | Corynebacterium acetoacidophilum ATCC 13870 | ala—glu | Corynebacterium acetoacidophilum AJ 12419 (FERM BP-2206) |
| Lysine | Brevibacterium lactofermentum AJ 3445 (FERM P-1944) | val—glu | Brevibacterium lactofermentum AJ 12420 (FERM BP-2207) |
| | Corynebacterium glutamicum AJ 3399 (FERM P-1615) | ala—glu | Corynebacterium glutamicum AJ 12421 (FERM BP-2208) |
| Arginine | Brevibacterium flavum AJ 3401 (FERM P-1642) | tyr—glu | Brevibacterium flavum AJ 12422 (FERM BP-2209) |
| Glutamic acid | Brevibacterium lactofermentum ATCC 13869 | tyr—glu | Brevibacterium lactofermentum AJ 12423 (FERM BP-2210) |
| | Corynebacterium glutamicum ATCC 13032 | ala—glu | Corynebacterium glutamicum AJ 12424 (FERM BP-2211) |
| Histidine | Brevibacterium flavum AJ 3620 (FERM P-2316) | trp—glu | Brevibacterium flavum AJ 12425 (FERM BP-2212) |
| | Corynebacterium glutamicum AJ 12092 (FERM P-7273) | glu—his | Corynebacterium glutamicum AJ 12426 (FERM BP-2213) |
| Proline | Brevibacterium flavum AJ 11512 (FERM P-5332) | tyr—glu | Brevibacterium flavum AJ 12427 (FERM BP-2214) |
| Isoleucine | Brevibacterium flavum AJ 3686 (FERM P-2433) | ala—asp | Brevibacterium flavum AJ 12428 (FERM BP-2215) |

TABLE 3

| | Peptide | | | | | | | |
|---|---|---|---|---|---|---|---|---|
| Gln | tyr—glu (%) | | | | ala—glu (%) | | | |
| Strain | 0 | 0.05 | 0.1 | 0.3 | 0 | 0.05 | 0.1 | 0.3 |
| Brevibacterium flavum ATCC 14067 | 100 | 85 | 45 | 0 | | | | |
| Brevibacterium flavum AJ 12418 | 100 | 100 | 100 | 72 | | | | |
| Corynebacterium acetoacidophilum ATCC 13870 | | | | | 100 | 70 | 30 | 0 |
| Corynebacterium acetoacidophilum AJ 12419 | | | | | 100 | 100 | 100 | 65 |

TABLE 4

| Lys* | Peptide | | | | | | | |
|---|---|---|---|---|---|---|---|---|
| | val—glu (%) | | | | ala—glu (%) | | | |
| Strain | 0 | 0.05 | 0.1 | 0.3 | 0 | 0.05 | 0.1 | 0.3 |
| Brevibacterium lactofermentum AJ 3445 | 100 | 95 | 80 | 10 | | | | |
| Brevibacterium lactofermentum AJ 12420 | 100 | 100 | 100 | 90 | | | | |
| Corynebacterium glutamicum AJ 3399 (FERM P-1615) | | | | | 100 | 50 | 10 | 0 |
| Corynebacterium glutamicum AJ 2421 | | | | | 100 | 100 | 100 | 100 |

*When Corynebacterium glutamicum was used, 15 mg/dl of methionine was supplemented.

TABLE 5

| Arg* | Peptide tyr—glu (%) | | | |
|---|---|---|---|---|
| Strain | 0 | 0.05 | 0.1 | 0.3 |
| Brevibacterium flavum AJ 3401 | 100 | 100 | 30 | 0 |
| Brevibacterium flavum AJ 12422 | 100 | 100 | 100 | 95 |

*Liquid medium was supplemented with 5 mg/dl of guanine.

TABLE 6

| Glu | Peptide | | | | | | | |
|---|---|---|---|---|---|---|---|---|
| | tyr—glu (%) | | | | ala—glu (%) | | | |
| Strain | 0 | 0.05 | 0.1 | 0.3 | 0 | 0.05 | 0.1 | 0.3 |
| Brevibacterium lactofermentum ATCC 13869 | 100 | 78 | 142 | 0 | | | | |
| Brevibacterium lactofermentum AJ 12423 | 100 | 100 | 95 | 80 | | | | |
| Corynebacterium glutamicum ATCC 13032 | | | | | 100 | 75 | 40 | 0 |
| Corynebacterium glutamicum AJ 12424 | | | | | 100 | 100 | 100 | 94 |

TABLE 7

| His | Peptide | | | | | | | |
|---|---|---|---|---|---|---|---|---|
| | trp—glu (%) | | | | glu—his (%) | | | |
| Strain | 0 | 0.05 | 0.1 | 0.3 | 0 | 0.05 | 0.1 | 0.3 |
| Brevibacterium flavum AJ 3620 | 100 | 100 | 75 | 36 | | | | |
| Brevibacterium flavum AJ 12425 | 100 | 100 | 100 | 100 | | | | |
| Corynebacterium glutamicum AJ 12092 | | | | | 100 | 100 | 96 | 55 |
| Corynebacterium glutamicum AJ 12426 | | | | | 100 | 100 | 100 | 98 |

TABLE 8

| Pro* | Peptide tyr—glu (%) | | | |
|---|---|---|---|---|
| Strain | 0 | 0.05 | 0.1 | 0.3 |
| Brevibacterium flavum AJ 11512 | 100 | 90 | 30 | 0 |
| Brevibacterium flavum AJ 12427 | 100 | 100 | 95 | 60 |

*Liquid medium was supplemented with 15 mg/dl of isoleucine.

TABLE 9

| Ile | Peptide ala—asp (%) | | | |
|---|---|---|---|---|
| Strain | 0 | 0.05 | 0.1 | 0.3 |
| Brevibacterium flavum AJ 3686 | 100 | 70 | 20 | 0 |
| Brevibacterium flavum AJ 12428 | 100 | 100 | 98 | 70 |

Example 1.

An aqueous solution medium having a composition of 10% of glucose, 1% of ammonium sulfate, 0.25% of potassium primary phosphate (KH$_2$PO$_4$), 0.04% of magnesium sulfate, 0.001% of ferrous sulfate, 350 µg/l of thiamine hydrochloride, 5 µg/l of biotin and 0.5 ml/dl of Aji-Eki® which is a soybean protein hydrolysate which accelerates the growth of L-amino acid-producing microorganisms and shortens the required culture time, at pH 7.0, was charged in an amount of 300 ml into separate small sized glass jar fermenters. After sterilizing in a conventional manner, the various L-glutamine-producing bacterial strains shown in Table 10, which had been previously grown in bouillon slants at 30° C. for 24 hours, were inoculated thereon. Then, incubation was carried out at 31.5° C. for 30 hours at 1200 rpm at an aeration rate of ¼ volume per minute, while keeping the pH at 6.5 by the addition of ammonia gas. After completion of the fermentation, the yield of L-glutamine produced and accumulated in the solution based on glucose was determined and is shown in Table 10.

TABLE 10

| Strain | Property | Yield of L-Glutamine Based on Glucose (%) |
| --- | --- | --- |
| Brevibacterium flavum AJ 14067 | Wild | 29.0 |
| Brevibacterium flavum AJ 12418 | Imparted with tyr—glu resistance | 40.0 |
| Corynebacterium acetoacidophilum ATCC 13870 | Wild | 22.5 |
| Corynebacterium acetoacidophilum AJ 12419 | Imparted with ala—glu resistance | 34.0 |

The cells were removed from 1 liter of the solution obtained after completion of the fermentation using Brevibacterium flavum AJ 12418 by centrifugation to give a supernatant. From the supernatant, L-glutamine was isolated in a conventional manner using an ion exchange resin to give 19.0 g of L-glutimine as crystals.

Example 2.

An aqueous solution medium having a composition of 10% of glucose, 2% of ammonium sulfate, 0.1% of potassium primary phosphate, 0.04% of magnesium sulfate, 0.001% of ferrous sulfate, 200 µg/l of thiamine hydrochloride, 500 µg/l of biotin, 5 ml/dl of Aji-Eki®, 1 mg/dl of nicotinamide and 0.1% of DL-alanine, at pH 7.0, was charged in an amount of 300 ml into separate small sized glass jar fermenters. After sterilizing in a conventional manner, the various L-lysine-producing bacterial strains shown in Table 11, which had been previously grown in bouillon slants at 30° C. for 48 hours, were inoculated thereon. Then, incubation was carried out at 31.5° C. for 48 hours at 1200 rpm at an aeration rate of ½ volume per minute, while keeping the pH at 7.0 by the addition of ammonia gas. After completion of the fermentation, the yield of L-lysine produced and accumulated in the solution based on glucose was determined and is shown in Table 11.

TABLE 11

| Strain | Property* | Yield of L-Lysine Based on Glucose (%) |
| --- | --- | --- |
| Brevibacterium lactofermentum AJ 3445 | AEC resistance | 16.0 |
| Brevibacterium lactofermentum AJ 12420 | Imparted with val—glu resistance | 31.0 |
| Corynebacterium glutamicum AJ 3399 | met, AEC resistance | 23.0 |
| Corynebacterium glutamicum AJ 12421 | Imparted with ala—glu resistance | 32.0 |

*AEC = S-(β-aminoethyl)-cystein.

The cells were removed from 1 liter of the solution obtained after completion of the fermentation using Brevibacterium lactofermentum AJ 12420 by centrifugation to give a supernatant. From the supernatant, L-lysine was isolated in a conventional manner using an ion exchange resin to give 19.2 g of L-lysine as crystals.

Example 3.

An aqueous solution medium having a composition of 10% of glucose, 4% of ammonium sulfate, 0.1% of potassium primary phosphate, 0.04% of magnesium sulfate, 0.001% of ferrous sulfate, 0.001% of manganese sulfate, 100 µg/l of thiamine hydrochloride, 100 µg/l of biotin, 5 ml/dl of Aji-Eki® and 0.2% of yeast extract, at pH 7.0, was charged in an amount of 300 ml into separate small sized glass jar fermenters. After sterilizing in a conventional manner, the various L-arginine-producing bacterial strains shown in Table 12, which had been previously grown in bouillon slants at 30° C. for 24 hours, were inoculated thereon. Then, incubation was carried out at 31.5° C. for 48 hours at 1200 rpm at an aeration rate of ½ volume per minute, while keeping the pH at 7.0 by the addition of ammonia gas. After completion of the fermentation, the yield of L-arginine produced and accumulated in the solution based on glucose was determined and is shown in Table 12.

TABLE 12

| Strain | Property | Yield of L-Arginine Based on Glucose (%) |
| --- | --- | --- |
| Brevibacterium flavum AJ 3401 (FERM P-1642) | gua⁻, 2-thiazolyl-alanine resistance | 25.5 |
| Brevibacterium flavum AJ 12422 (FERM BP-2209) | Imparted with tyr—glu resistance | 32.0 |

The cells were removed from 1 liter of the solution obtained after completion of the fermentation using Brevibacterium flavum AJ 12422 by centrifugation to give a supernatant. From the supernatant, L-arginine was isolated in a conventional manner using an ion exchange resin to give 17.3 g of L-arginine as crystals.

Example 4.

An aqueous solution medium having a composition of 10% of glucose, 1% of ammonium sulfate, 0.2% of potassium primary phosphate, 0.1% of magnesium sulfate, 0.001% of ferrous sulfate, 0.001% of manganese sulfate, 500 µg/l of thiamine hydrochloride, 5 µg/l of biotin and 1 ml/dl of Aji-Eki®, at pH 7.2, was charged in an amount of 300 ml into separate small sized glass jar fermenters. After sterilizing in an autoclave, the various L-glutamic acid-producing bacterial strains shown in Table 13, which had been previously grown in bouillon slants at 30° C. for 24 hours, were inoculated thereon. Then, incubation was carried out at 31.5° C. for 48 hours at 1200 rpm at an aeration rate of ½ volume per minute, while keeping the pH at 7.2 by the addition of ammonia gas. After completion of the fermentation, the yield of L-glutamic acid produced and accumulated in the solution based on glucose was determined and is shown in Table 13.

TABLE 13

| Strain | Property | Yield of L-glutamic Acid Based on Glucose (%) |
| --- | --- | --- |
| Brevibacterium lactofermentum ATCC 13869 | Wild | 44.2 |
| Brevibacterium lactofermentum AJ 12423 | Imparted with tyr—glu resistance | 49.5 |
| Corynebacterium | Wild | 40.1 |

TABLE 13-continued

| Strain | Property | Yield of L-glutamic Acid Based on Glucose (%) |
|---|---|---|
| glutamicum ATCC 13032 | | |
| Corynebacterium glutamicum AJ 12424 | Imparted with ala—glu resistance | 46.8 |

The cells were removed from 1 liter of the solution obtained after completion of the fermentation using Brevibacterium lactofermentum AJ 12423 by centrifugation to give a supernatant. From the supernatant, L-glutamic acid was isolated in a conventional manner using an ion exchange resin to give 35.5 g of L-glutamic acid as crystals.

Example 5.

An aqueous solution medium having a composition of 10% of glucose, 0.5% of ammonium sulfate, 0.15% of potassium primary phosphate, 0.1% of magnesium sulfate, 0.001% of ferrous sulfate, 0.001% of manganese sulfate, 300 µg/l of thiamine hydrochloride, 350 µg/l of biotin, 5 ml/dl of Aji-Eki® and 0.5% of ammonium acetate, at pH 7.0, was charged in an amount of 300 ml into separate small sized glass jar fermenters. After sterilizing in an autoclave, the various L-histidine-producing bacterial strains shown in Table 14, which had been previously grown in bouillon slants at 30° C. for 24 hours, were inoculated thereon. Then, incubation was carried out at 31.5° C. for 48 hours at 1200 rpm at an aeration rate of ½ volume per minute, while keeping the pH at 6.5 by the addition of ammonia gas. After completion of the fermentation, the yield of L-histidine produced and accumulated in the solution based on glucose was determined and is shown in Table 14.

TABLE 14

| Strain | Property | Yield of L-Histidine Based on Glucose (%) |
|---|---|---|
| Brevibacterium flavum AJ 3620 | 2-AT, sulfadiazine, cobalamine resistance | 7.2 |
| Brevibacterium flavum AJ 12425 | Imparted with trp—glu resistance | 10.0 |
| Corynebacterium glutamicum AJ 12092 | 2-AT resistance | 5.0 |
| Corynebacterium glutamicum AJ 12426 | Imparted with glu—his resistance | 9.3 |

The cells were removed from 1 liter of the solution obtained after completion of the fermentation using Corynebacterium glutamicum AJ 12426 by centrifugation to give a supernatant. From the supernatant, L-histidine was isolated in a conventional manner using an ion exchange resin to give 4.7 g of L-histidine as crystals.

Example 6.

An aqueous solution medium having a composition of 10% of glucose, 4% of ammonium sulfate, 0.1% of potassium primary phosphate, 0.5% of magnesium sulfate, 0.001% of ferrous sulfate, 0.001% of manganese sulfate, 100 µg/l of thiamine hydrochloride, 350 µg/l of biotin, 1 ml/dl of Aji-Eki® and 35 mg/dl of L-isoleucine, at pH 7.0, was charged in an amount of 300 ml into separate small sized glass jar fermenters. After sterilizing in a conventional manner, the various L-proline-producing bacterial strains shown in Table 15, which had been previously grown in bouillon slants at 30° C. for 24 hours, were inoculated thereon. Then, incubation was carried out at 31.5° C. for 48 hours at 1200 rpm at an aeration rate of ½ volume per minute, while keeping the pH at 7.0 by the addition of ammonia gas. After completion of the fermentation, the yield of L-proline produced and accumulated in the solution based on glucose was determined and is shown in Table 15.

TABLE 15

| Strain | Property | Yield of L-Proline Based on Glucose (%) |
|---|---|---|
| Brevibacterium flavum AJ 11512 | ile$^-$, sulfaguanidine resistance | 21.0 |
| Brevibacterium flavum AJ 12427 | Imparted with tyr—glu resistance | 29.0 |

The cells were removed from 1 liter of the solution obtained after completion of the fermentation using Brevibacterium flavum AJ 12427 by centrifugation to give a supernatant. From the supernatant, L-proline was isolated in a conventional manner using an ion exchange resin to give 17.5 g of L-proline as crystals.

Example 7.

An aqueous solution medium having a composition of 10% of glucose, 1% of ammonium sulfate, 0.1% of potassium primary phosphate, 0.04% of magnesium sulfate, 0.001% of ferrous sulfate, 0.001% of manganese sulfate, 100 µg/l of thiamine hydrochloride, 100 µg/l of biotin and 2 ml/dl of Aji-Eki®, at pH 7.0, was charged in an amount of 300 ml into separate small sized glass jar fermenters. After sterilizing in a conventional manner, the various L-isoleucine-producing bacterial strains shown in Table 16, which had been previously grown in bouillon slants at 30° C. for 24 hours, were inoculated thereon. Then, incubation was carried out at 31.5° C. for 48 hours at 1200 rpm at an aeration rate of ½ volume per minute, while keeping the pH at 7.3 by the addition of ammonia gas. After completion of the fermentation, the yield of L-isoleucine produced and accumulated in the solution based on glucose was determined and is shown in Table 16.

TABLE 16

| Strain | Property* | Yield of L-Isoleucine Based on Glucose (%) |
|---|---|---|
| Brevibacterium flavum AJ 3686 | AHV resistance | 8.5 |
| Brevibacterium flavum AJ 12428 | Imparted with ala—asp resistance | 13.0 |

*AHV = α-amino-β-hydroxy-valeric acid.

The cells were removed from 1 liter of the solution obtained after completion of the fermentation using Brevibacterium flavum AJ 12428 by centrifugation to give a supernatant. From the supernatant, L-isoleucine was isolated in a conventional manner using an ion exchange resin to give 6.5 g of L-isoleucine as crystals.

Thus, as shown by the results given above, according to the present invention, various L-amino acids can be obtained in a good yield.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for producing an L-amino acid, which comprises culturing a mutant L-amino acid producing microorganism belonging to a genus selected from Brevibacterium and Corynebacterium which is resistant to a dipeptide at a concentration of 0.3% in a liquid medium for a time sufficient to produce said L-amino acid; and recovering said L-amino acid produced wherein 1) L-glutamine is produced from a tyr-glu resistant mutant of *Brevibacterium flavum* ATCC 14067 or an ala-glu resistant mutant of *Corynebacterium acetoacidophilum* ATCC 13870;
2) L-lysine is produced from a val-glu resistant mutant of *Brevibacterium lactofermentum* ATCC 13869 or an ala-glu resistant mutant of *Corynebacterium glutamicum* ATCC 13032;
3) L-arginine is produced from a tyr-glu resistant mutant of *Brevibacterium flavum* ATCC 14067;
4) L-glutamic acid is produced from a tyr-glu resistant mutant of *Brevibacterium lactofermentum* ATCC 13869 or an ala-glu resistant mutant of *Corynebacterium glutamicum* ATCC 13032;
5) L-histidine is produced from a trp-glu resistant mutant of *Brevibacterium flavum* ATCC 14067 or a glu-his resistant mutant of *Corynebacterium glutamicum* ATCC 13032;
6) L-proline is produced by a tyr-glu resistant mutant of *Brevibacterium flavum* ATCC 14067; and
7) L-isoleucine is produced from an ala-asp resistant mutant of *Brevibacterium flavum* ATCC 14067, and wherein said mutant microorganism is obtained by mutation of a parent strain, and said microorganism produces the L-amino acid in an amount greater than the amount produced by the parent strain.

2. The process of claim 1, wherein said L-amino acid producing microorganism is obtained by contacting the parent strain with N-methyl-N'-nitro-N-nitrosoguanidine.

3. A process for producing an L-amino acid, which comprises culturing a mutant L-amino acid producing microorganism belonging to the genus Brevibacterium which is resistant to a dipeptide at a concentration of 0.3% in a liquid medium for a time sufficient to produce said L-amino acid; and recovering said L-amino acid produced, wherein the amino acid is L-glutamine, the mutant microorganism is a tyr-glu resistant mutant of *Brevibacterium flavum* ATCC 14067, the mutant microorganism is obtained by mutation of a parent strain, and the mutant microorganism produces the L-amino acid in an amount greater than the amount produced by the parent strain.

4. The process of claim 3, wherein said L-amino acid producing microorganism is obtained by contacting the parent strain with N-methyl-N'-nitro-N-nitrosoguanidine.

* * * * *